United States Patent [19]

Williams, Jr.

[11] 4,134,404
[45] Jan. 16, 1979

[54] PORTABLE COLOSTOMY KIT

[76] Inventor: Clarence B. Williams, Jr., 2009 Broad St., Tallahassee, Fla. 32301

[21] Appl. No.: 792,416

[22] Filed: Apr. 29, 1977

[51] Int. Cl.² ............................................. A61F 5/44
[52] U.S. Cl. ........................................... 128/283; 4/1
[58] Field of Search ....................... 128/283, 227; 4/1

[56] References Cited

U.S. PATENT DOCUMENTS

| | | | |
|---|---|---|---|
| 605,178 | 6/1898 | Ferguson | 128/227 |
| 2,223,566 | 12/1940 | Koch | 128/283 |
| 2,331,226 | 10/1943 | Pritchard | 128/283 |
| 2,438,073 | 3/1948 | Saur | 128/283 |
| 2,561,906 | 7/1951 | Clark | 128/283 |
| 2,568,857 | 9/1951 | Jacobs | 128/283 |
| 2,639,711 | 5/1953 | Smith | 128/283 |
| 2,689,567 | 9/1954 | Welch | 128/283 |
| 2,782,785 | 2/1957 | Arcano | 128/283 |
| 2,869,547 | 1/1959 | Yohe | 128/283 |
| 3,672,370 | 6/1972 | Marsan | 128/283 |

OTHER PUBLICATIONS

Tinklepaugh, Irene; *A New Colostomy Set*, In Amer. Jour. of Nursing, vol. 51, Nov. 1951.

*Primary Examiner*—Robert W. Michell
*Assistant Examiner*—Arthur S. Rose
*Attorney, Agent, or Firm*—Berman, Aisenberg & Platt

[57] ABSTRACT

A colostomy kit which features a small, portable waste receptacle adapted to be strapped about the waist of the user. The kit includes a removable cover having an integrally formed inlet conduit with a self-contained control valve. The conduit may be connected to a flushing water supply provided by one side of a unique dual-supply container. The other portion of the container may house a relatively hot irrigation fluid. The second container is preferably provided with a separate catheter outlet, and is insulated from the cooler waste flushing water in the adjacent, first compartment.

3 Claims, 7 Drawing Figures

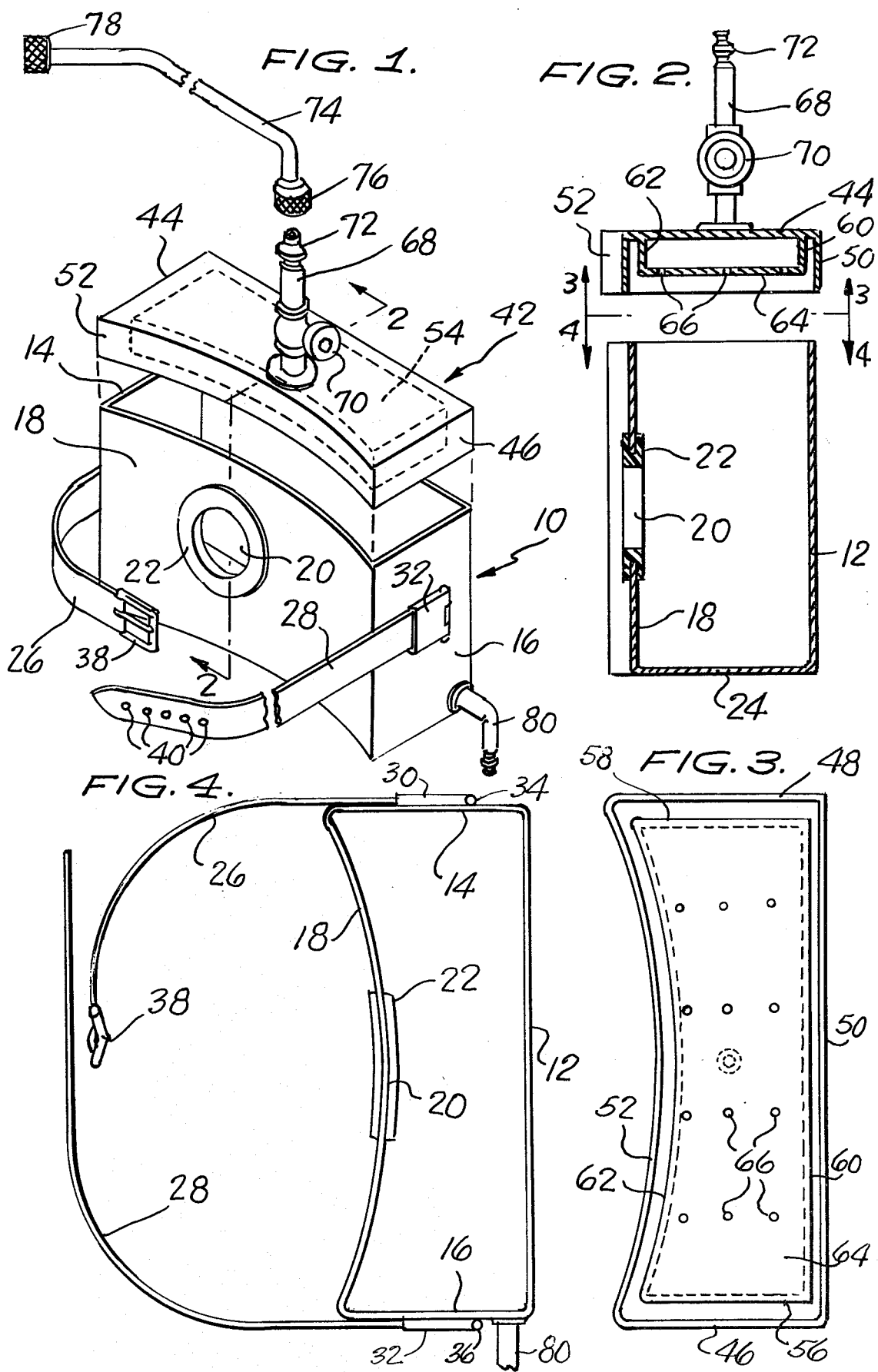

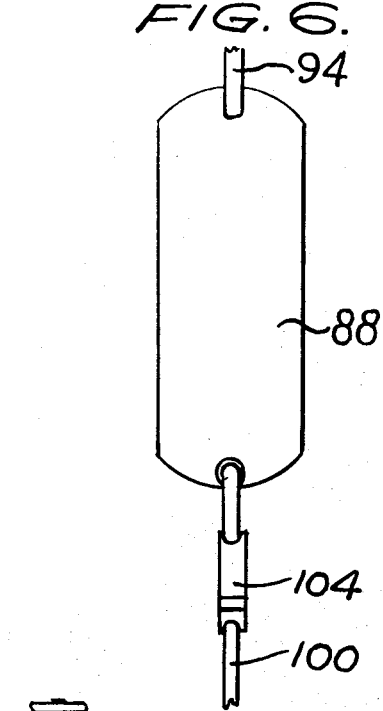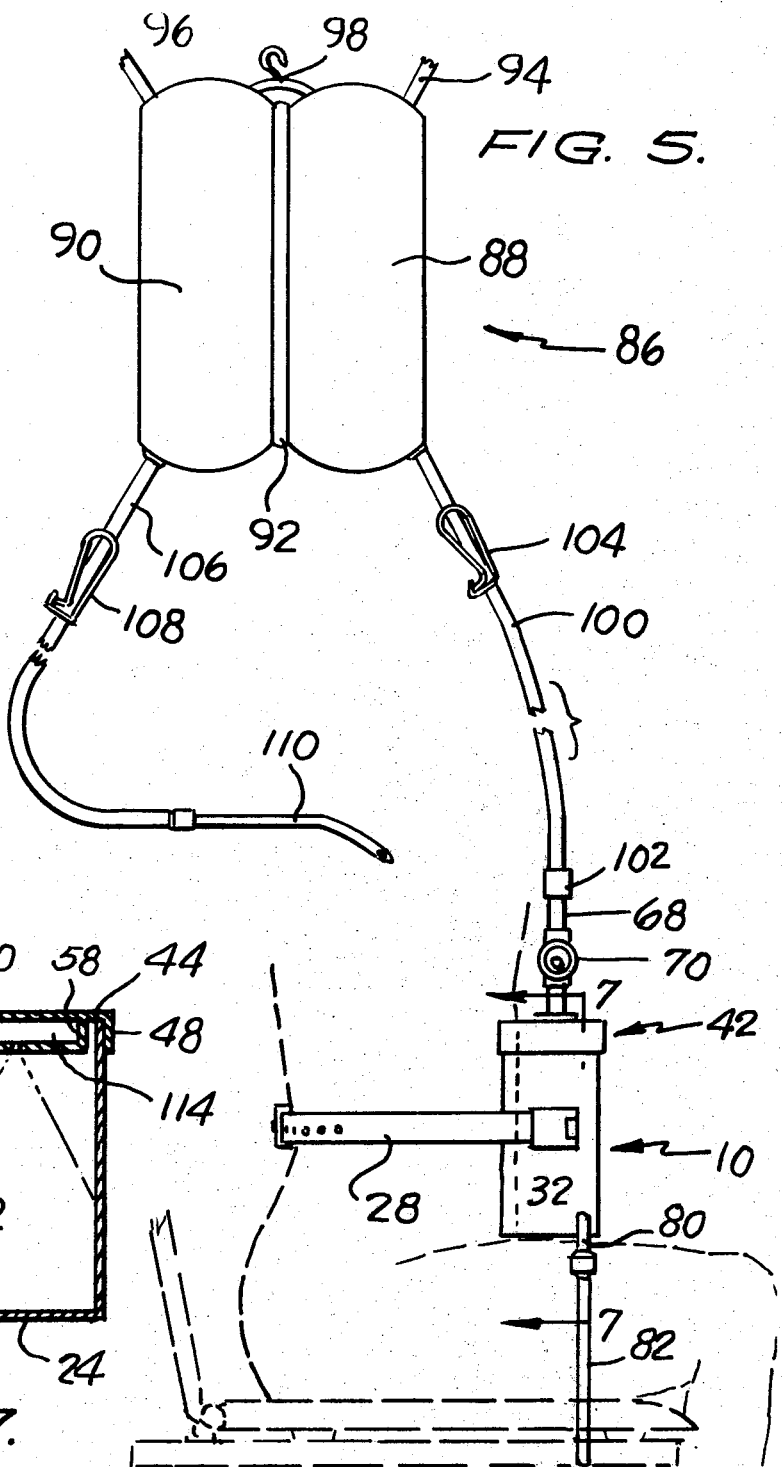

PORTABLE COLOSTOMY KIT

BACKGROUND OF THE INVENTION

1. Field of the Invention

This invention is related generally to a colostomy toilet and, more particularly, is directed towards a colostomy kit which is composed of relatively inexpensive, compact, easily transported and therefore portable components.

2. Description of The Prior Art

A colostomy is a surgical orifice or opening from the colon through the abdominal wall which results in the formation of an artifical anus. When such an operation is performed, the colon or a portion thereof is removed. As a result, normal evacuation of the bowels is impossible. Colostomy patients are therefore required to perform this normal bodily function by means of various irrigation devices and receptacles designed to supplant such function. Such devices abound in the prior art.

For example, my own earlier U.S. Pat. No. 2,864,094 teaches a colostomy toilet connected to the wall for use in the home or hospital. The toilet includes a hose attached to an irrigation pipe for cleaning the toilet, the other end of the hose being connected to a source of flushing fluid under pressure, such as the cold water supply of the home.

U.S. Pat. No. 2,782,785 teaches a colostomy washing device which includes a flushing head that receives water through a hose. A perforated V-shaped spray plate converts the water supply into a spray which is, in turn, directed angularly against the walls of the bag as it is held suspended over the toilet for cleaning purposes.

U.S. Pat. No. 2,767,713 illustrates a colostomy applicator comprising a casing which includes a belt to position the circular opening over the colostomy in the abdomen of the patient.

U.S. Pat. No. 2,223,566 illustrates the utilization of a douche bag containing an irrigating fluid, the outlet from the bag being connected to a catheter via a control valve. Discharge from a domestic water faucet may be utilized to flush the receptacle after irrigation has been effectuated.

Other prior art U.S. patents in this same general area of which I am aware include: U.S. Pat. Nos. 2,869,547; 3,672,370; 3,690,320; 3,718,141; 3,789,846; 3,830,235; 3,910,274; and 3,941,133.

While such devices are generally useful, they are, as a whole, generally too complex to use and clean properly, which can lead to unsatisfactory unsanitary conditions. Further, many of the prior art devices are bulky, expensive, and not easily transportable.

Further, the prior art devices are deficient in failing to provide convenient means for providing both the necessary flushing water, and the hot, irrigating fluid for the colostomy.

It towards overcoming the foregoing disadvantages that the present invention is advanced.

OBJECTS AND SUMMARY OF THE INVENTION

It is therefore a primary object of the present invention to provide a colostomy kit which overcomes all of the disadvantages noted above with respect to the prior art devices.

Another object of the present invention is to provide a colostomy kit which is portable, self-contained, has a minimum number of elements and moving parts, is easily transportable, easy to clean, sanitary, and may be constructed at minimum expense.

A further object of the present invention is to provide a colostomy kit which may be utilized quite comfortably by the patient while sitting on a toilet, and which provides means for adjusting the fit thereof to the abdomen as well as the water flow for both flushing and irrigation purposes.

An additional object of the present invention is to provide a portable colostomy kit which includes a unique dual-bag container for housing the irrigating fluid as well as the flushing fluid.

Another object of the present invention is to provide a colostomy kit which includes a waste receptacle that is continuously sprayed with water during elimination and which may be easily washed and disinfected after each use.

The foregoing and other objects are attained in accordance with one aspect of the present invention through the provision of a colostomy kit, which comprises a waste receptacle having one wall contoured to fit the abdomen of a user, an opening in said wall which is sized to fit about the colostomy of the patient, means connected to the waste receptacle for fastening same about the user, cover means positionable on the waste receptacle and having an inlet conduit formed therein, and means for containing a first fluid and a second fluid. Means are also provided which connect the containing means to the inlet conduit for flushing the waste receptacle with the first fluid, and means extend from the containing means for irrigating the colostomy with the second, normally hot fluid.

In accordance with more specific aspects of the present invention, the containing means comprises a first bag for containing the first fluid, a second bag for containing the second fluid, and means for joining the first bag with the second bag which also comprise means for thermally insulating the two bags from one another. Means may also be connected to the dual-bag containing means for hanging same at a certain height whereby the first and second fluids will respectively be delivered from the two bags under the force of gravity. Each of the bags may be provided with its own inlet for refilling same.

In accordance with other aspects of the present invention, the colostomy irrigating means may comprise a flexible hose connected at one end to the second bag and which terminates at its distal end in a catheter. The fastening means may comprise first and second flexible straps each connected at one end thereof to an opposed side wall of the waste receptacle via a pair of hinges, the distal ends of the straps terminating in a belt buckle pair for selectively coupling same together. The inlet conduit preferably also includes its own, separately operable valve means for permitting control of the flow of the first, flushing fluid therethrough.

Also in accordance with the present invention, means may be formed integrally with the cover means and disposed under the inlet conduit thereof for dispersing the first fluid onto the inner walls of the waste receptacle, the dispersing means comprising in a preferred form a perforated plate positioned substantially parallel with the cover means and connected thereto via substantially vertical side walls that extend about the entire periphery thereof.

BRIEF DESCRIPTION OF THE DRAWINGS

Various objects, features and attendant advantages of the present invention will be more fully appreciated as the same becomes better understood from the following detailed description of the present invention when considered in connection with the accompanying drawings, in which:

FIG. 1 is a perspective, rear view, partially exploded, which illustrates a preferred embodiment of one component of the colostomy kit of the present invention;

FIG. 2 is a cross-sectional view of the preferred embodiment component illustrated in FIG. 1 and taken along line 2—2 thereof;

FIG. 3 is an underside, plan view of a preferred embodiment of the cover means of the present invention which is as viewed along line 3—3 of FIG. 2;

FIG. 4 is a top, plan view of a preferred embodiment of the waste receptacle component of the present invention as viewed along line 4—4 of FIG. 2;

FIG. 5 is a schematic illustration of preferred embodiments of several additional components of the colostomy kit of the present invention, illustrated during one possible mode of useage;

FIG. 6 is a side view of one of the components of the preferred embodiment illustrated in FIG. 5; and FIG. 7 is a sectional view of certain of the components of the preferred embodiment illustrated in FIG. 5 and taken along line 7—7 thereof, which also illustrates an alternative source of supply thereto.

DETAILED DESCRIPTION OF THE PREFERRED EMBODIMENTS

Referring now to the drawings, wherein like reference numerals designate identical or corresponding parts throughout the several views, and more particularly to FIGS. 1 through 4 thereof, there is illustrated therein a preferred embodiment of one component of the portable colostomy kit of the present invention. The component illustrated in FIGS. 1 through 4 comprises a waste receptacle which is indicated generally by the reference numeral 10.

Waste receptacle 10 comprises a container having a front wall 12 and a pair of side walls 14 and 16. Walls 12, 14 and 16 are preferably substantially planar, the side walls being parallel to one another and extending perpendicularly from front wall 12.

Extending between the side walls 14 and 16 at the distal portions thereof is a curved rear wall 18 which is contoured so as fit the abdomen of the colostomy patient. Centrally formed on the rear wall 18 of receptacle 10 is an aperture or opening 20 which is designed so as to fit about the colostomy of the patient. A substantially circular grommett or bushing 22 may include an outer annular groove for fitting within the opening 20 (see FIG. 2). The construction of the receptacle is completed by the provision of a substantially planar bottom plate 24 which extends between the front, side and rear walls 12, 14, 16 and 18.

A pair of straps 26 and 28 are secured to the side walls 14 and 16 of receptacle 10 via a pair of hinges 30 and 32, respectively. Hinges 30 and 32 are preferably pivotally connected to side walls 14 and 16 by a pair of pivots 34 and 36, respectively, which permit the straps 26 and 28 to be extended outwardly from the receptacle 10 in order to fit the patient.

Strap 26 terminates in a standard belt buckle 38, while strap 28 has a plurality of perforations 40 formed in its free end to permit straps 26 and 28 to form an adjustable belt so that the receptacle 10 may be adjustably fit about the abdomen and waist of the patient.

Still with reference to FIGS. 1 through 4, the colostomy kit of the present invention also preferably includes a lid which is indicated generally by reference numeral 42. The lid 42 includes a top wall 44, which is preferably substantially planar. Extending downwardly from the outer edges of top wall 44 are side walls 46 and 48, front wall 50, and rear wall 52, all of which are shaped congruently to the corresponding walls of receptacle 10, which permits the lid 42 to be snugly fit about the top of receptacle 10.

Downwardly depending from the top wall 44 of lid 42 and shaped congruently with respect to the side, front and rear walls of the latter is a spray-generating member which is indicated generally by reference numeral 54. Member 54 includes a pair of side walls 56 and 58 which depend downwardly from top wall of lid 42, as do a front wall 60 and a rear wall 62. Extending between the walls 56, 58, 60 and 62, and positioned substantially parallel to the top wall 44, is a lower plate 64 having a plurality of spaced perforations or apertures 66 positioned therethrough, the purpose of which will become more clear hereinafter.

Centrally opening into the top wall 44 of lid 42 is an inlet conduit 68 which preferably has a hand operable valve 70 provided therewith. The free end of conduit 68 has a simple threaded male member 72, or the like, for connection to an intermediate conduit 74 (FIG. 1). Conduit 74 is preferably provided with a pair of knurled connecting nuts 76 and 78 at either end thereof for facilitating connection to member 72 and to a source of water, respectively.

Finally, provided in the lower portion of waste receptacle 10, such as on side wall 16 thereof, is a waste outlet conduit 80. As may be seen by referring now to FIG. 5, a flexible hose 82 may be coupled to the waste outlet conduit 80 for delivering the outlet fluid and waste to the toilet 84. Alternatively and clearly, the individual wearing the waste receptacle 10 could just as easily sit on the toilet 84 as stand therenext as illustrated in FIG. 5.

FIG. 5 illustrates yet another component of the colostomy kit of the present invention which is indicated generally by reference numeral 86 and comprises a dual-bag container unit. The dual-bag unit 86 is comprised of two compartments 88 and 90 which are separated by an insulation separator 92 in the form of thermal insulation.

Compartments 88 and 90 each include a separate inlet 94 and 96, respectively, for filling same, and the entire dual-bag unit 86 may be supported by a hanger or hook support 98 connected thereto.

Compartment 88 has an outlet conduit 100 extending from the lower portion thereof and in communication with the contents thereof. Outlet conduit 100 may be coupled via a connector 102 to the inlet conduits 68 of the lid 42 of the waste receptacle 10. A clamp 104 is also preferably provided on the outlet conduit 100, the latter of which may be a flexible hose or the like. Compartment 88 is designed to hold the cleaning or flushing water, which is generally at a temperature of about 60° F. The flushing water leaves compartment 88 to waste receptacle 10 under the force of gravity and may be controlled by clamp 104 as well as valve 70.

Adjacent compartment 90, on the other hand, is designed to house the relatively hot (110° F.) water for colostomy irrigation purposes. Extending downwardly from compartment 90 is an irrigation outlet conduit 106, which may also be in the form of a flexible hose or the like. A clamp 108 for control purposes may also be provided, and conduit or hose 106 terminates in a catheter 110. The catheter 110 may be utilized to direct the hot irrigating fluid from compartment 90 into the colostomy of the patient via opening 20 in receptacle 10 after the cover 42 has been removed therefrom.

An alternative source of supply fluid is illustrated in FIG. 7 and is seen to simply comprise the city's source of tap water which may be fed via a hand operated faucet 118 and flexible hose 116 to the inlet conduit 68 of the waste receptacle 10. As may be appreciated from FIG. 7, in operation, during periods of elimination, the valve 70 is opened to deliver a constant flow of water through orifice 112 which is formed in the top wall 44 of the lid 42. The perforated plate 64 defines a chamber 114 which begins to fill with the fluid and directs same via perforations or apertures 66 onto the inner side walls of receptacle 10 so as to flush the waste delivered through opening 20 out through waste outlet 80.

It is seen that I have provided a compact, inexpensive and easily transported colostomy kit which may be sanitarily utilized by an individual in either a sitting or standing position. The belt 28 (FIG. 5) frees the hands of the user for other purposes. The constant water spraying provided by perforated plate 64 helps eliminate odors generated by the colostomy discharge. The receptacle features a self-contained valve 70 which provides a convenient water flow control, the latter of which may be provided by either the city water supply or a suspended reservoir, which may be comprised, for example, of plastic. The dual-bag assembly 86 has insulation between the two water supplies to prevent temperature transfer between the irrigation solution and the flushing solution.

The receptacle of the present invention may be seen to be self-scouring and is easily disassembled after use for scouring and disinfection. The flexible hoses and knurled nut design provides for easy assembly and disassembly, as well as leak-proof connections to further facilitate useage of the kit.

Obviously, numerous modifications and variations of the present invention are possible in light of the above teachings. Therefore, within the scope of the appended claims, the invention may be practiced otherwise than as specifically described herein.

I claim as my invention:

1. A colostomy kit, which comprises:

a relatively small, portable waste receptacle open at the top and having parallel planar side walls and a rear wall extending between said side walls and curved so as to fit adjacent the abdomen of a user;

a substantially circular opening in said rear wall sized to fit about a colostomy of the user;

belt means pivotally mounted to said side walls for fastening said waste receptacle about the user;

a removable cover having a substantially planar top wall with an inlet conduit formed therein and side walls shaped proportionately to those of said waste receptacle so as to be fitted over said open top in such a manner that the side walls of said cover are positioned on the outside of the side walls of said receptacle;

a fluid container unit comprising a first compartment for containing a relatively cool flushing fluid, a second compartment for containing a relatively hot irrigating fluid, and thermal insulation positioned between and joining said first and second compartments;

a hanger connected to said fluid container unit to permit said flushing and irrigating fluids to be delivered therefrom by gravity;

a first hose connected between said first compartment and said inlet conduit on said cover for delivering flushing fluid to said receptacle;

a second hose connected to said second compartment and not connected to said first hose, said second hose terminating in a catheter for directing irrigating fluid into said colostomy; and a substantially planar perforated plate positioned parallel to and underneath said top wall of said removable cover, said plate being connected to said top wall by vertical side walls that are shaped proportionately to said side walls of said cover and which are positioned in use on the inside of the side walls of said receptacle so as to form a substantially closed chamber for receiving flushing fluid from said inlet conduit and for directing same to the inner surfaces of said waste receptacle.

2. A colostomy kit as set forth in claim 1, further comprising first and second inlet means disposed respectively at the top of said first and second compartments for admitting flushing and irrigating fluids thereto, respectively.

3. A colostomy kit as set forth in claim 1, further comprising valve means operatively coupled to said inlet conduit for controlling the flow of said flushing fluid therethrough.

* * * * *